US007041113B2

(12) United States Patent
Gruhl et al.

(10) Patent No.: US 7,041,113 B2
(45) Date of Patent: May 9, 2006

(54) MINIMAL INVASIVE ENDOSCOPIC METHODS AND APPARATUS FOR HARVESTING BLOOD VESSELS

(75) Inventors: Frederick Gruhl, Ann Arbor, MI (US); Erin Jessica Lindsay, Manchester, MI (US)

(73) Assignees: Terumo Corporation, Tokyo (JP); Olympus Optical Company, Ltd., Hachioji (JP)

( * ) Notice: Subject to any disclaimer, the term of this patent is extended or adjusted under 35 U.S.C. 154(b) by 453 days.

(21) Appl. No.: 10/139,367

(22) Filed: May 7, 2002
(Under 37 CFR 1.47)

(65) Prior Publication Data
US 2003/0212420 A1 Nov. 13, 2003

(51) Int. Cl.
*A61B 17/28* (2006.01)
*A61B 17/32* (2006.01)

(52) U.S. Cl. .................. 606/159; 606/167; 606/170; 606/205; 606/206

(58) Field of Classification Search .............. 606/108, 606/120, 142, 159, 174, 190, 205, 167, 170, 606/206; 600/104, 129; 128/898
See application file for complete search history.

(56) References Cited

U.S. PATENT DOCUMENTS 5,207,691 A * 5/1993 Nardella ................. 606/139
5,527,319 A * 6/1996 Green et al. ............. 606/139
5,792,135 A 8/1998 Madhani et al.
5,855,583 A 1/1999 Wang et al.
6,132,441 A 10/2000 Grace
6,206,903 B1 3/2001 Ramans
6,309,397 B1 10/2001 Julian et al.
6,312,435 B1 11/2001 Wallace et al.

OTHER PUBLICATIONS

Dziedzic, Ryan P. & Frecker, May I. "Design of Multifunctional Complaint Mechanisms for Minimally Invasive Surgery", Proceedings of DETEC'01—ASME 2001 Design Engineering Technical Conference, Pittsburgh, PA , Sep. 9-12, 2001 (pp. 441-450).
Schultz, Leonard S. et al., "Using 5-mm Bipolar Cutting Forceps: A New Multifunctional Instrument" Journal of Laparoendoscopic & Advanced Surgical Techniques (Dec. 6, 1997, pp. 375-378, vol. #6), Mary Ann Liebert, Inc, U.S.A.

* cited by examiner

*Primary Examiner*—Julian W. Woo
*Assistant Examiner*—Sarah Webb
(74) *Attorney, Agent, or Firm*—Buchanan Ingersoll PC

(57) ABSTRACT

A blood vessel in a patient is severed by inserting a shaft through an incision in the patient, the shaft carrying first and second clamps. The first and second clamps are closed against the vessel in closely adjacent relationship to one another. Thereafter, the clamps are moved in generally opposing directions to sever the vessel at a location between the clamps. Each clamp carries a cauterizing pad for cauterizing the severed ends of the vessel.

5 Claims, 6 Drawing Sheets

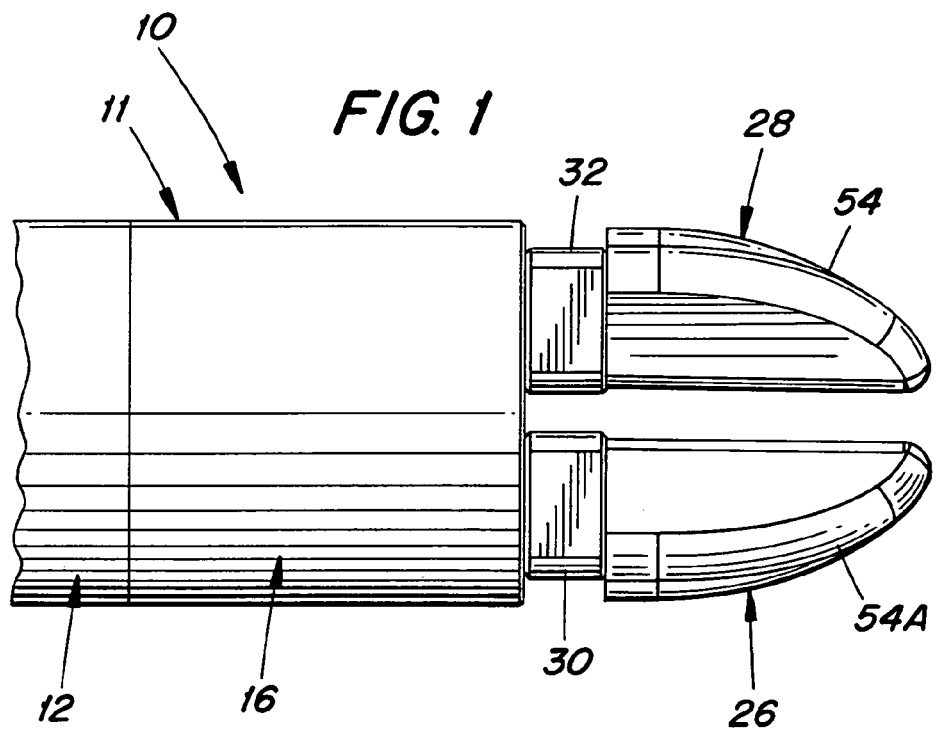
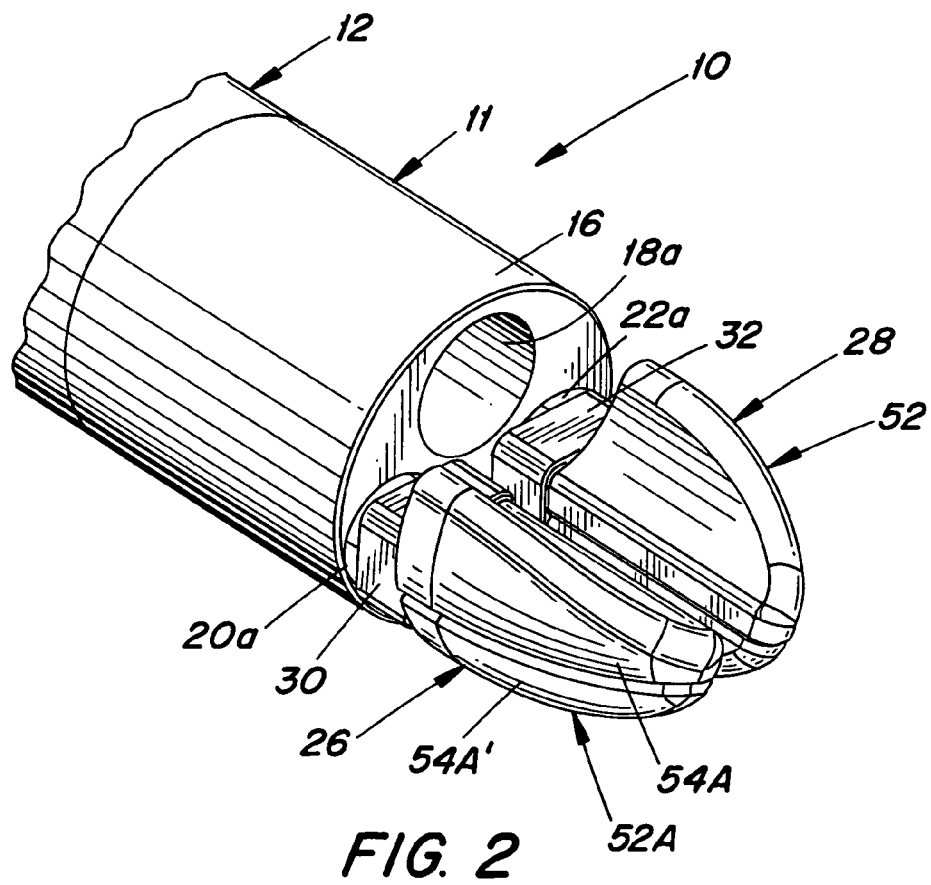

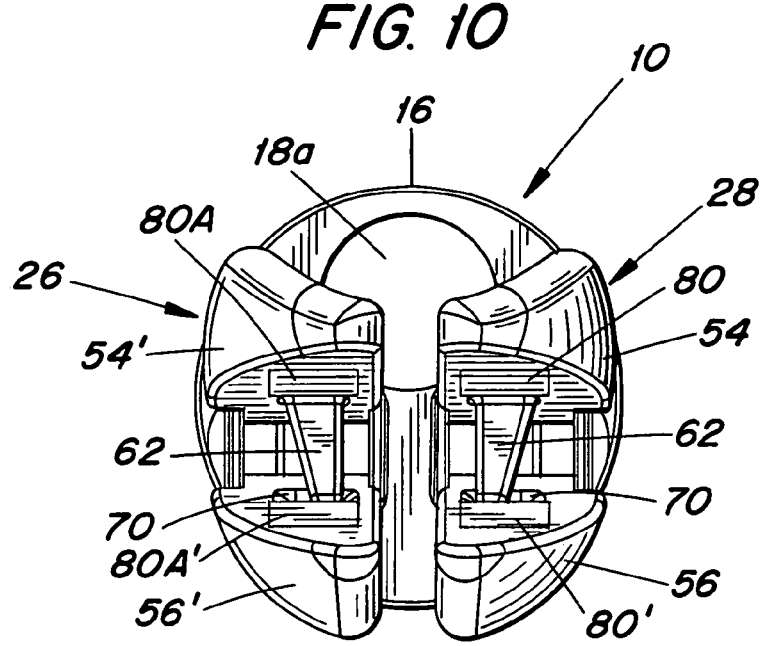
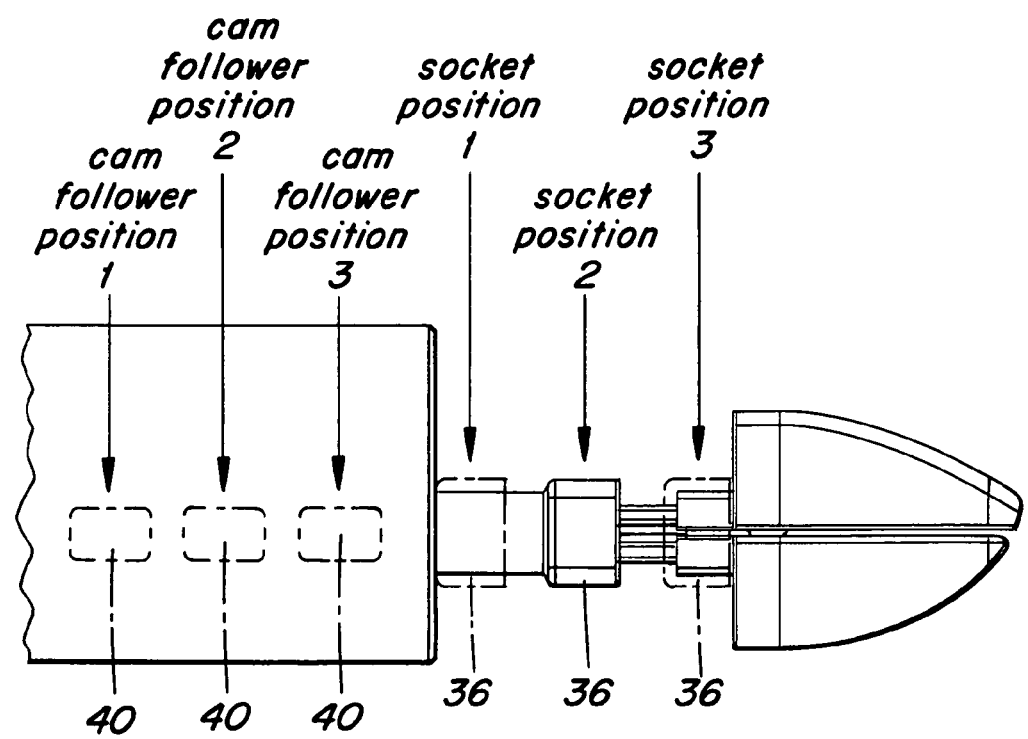

US 7,041,113 B2

MINIMAL INVASIVE ENDOSCOPIC METHODS AND APPARATUS FOR HARVESTING BLOOD VESSELS

BACKGROUND OF THE INVENTION

The present invention relates to coronary revascularization and in particular to methods and apparatus for harvesting sections of vascular vessels, such as saphenous veins.

For certain surgical procedures, such as coronary artery bypass grafting (CABG), a section of a vascular vessel such as a saphenous vein in a patient's leg is harvested and attached elsewhere to form a bypass between an arterial blood source and a coronary artery that is to be bypassed.

In an effort to reduce trauma to the patent, less-invasive vessel harvesting techniques have been developed which involve the use of an endoscope. In particular, a small incision is made in the patient's leg to enable the endoscope and surgical instruments to be inserted. For example, it is necessary to sever and cauterize side branches of the vessel section being harvested, and then sever and cauterize the ends of that vessel section. That procedure traditionally involves the withdrawal of one instrument and the insertion of another, which intensifies the trauma to the vessel and the surrounding tissue.

It would be desirable to enable vessel harvesting procedures to be carried out in a minimally invasive manner that further reduces trauma to the patient by minimizing the number of insertions/removals of surgical instruments.

SUMMARY OF THE INVENTION

The present invention relates to a method of severing a blood vessel in a patient, comprising the steps of:
  A. inserting a shaft through an incision in the patient, the shaft carrying first and second clamps;
  B. applying the first and second clamps to the vessel in closely adjacent relationship; and then
  C. moving the first and second clamps in generally opposite directions to stress and sever the vessel at a location between the clamps.

Preferably, the clamps carry cauterizing pads for cauterizing the severed vessel.

Preferably, step C is performed by moving the clamps in generally opposing directions along the axis of the vessel.

Another aspect of the present invention relates to an apparatus for severing a blood vessel. The apparatus includes a carrier shaft adapted to be inserted into a patient. First and second clamps are carried by the shaft. A displacement mechanism is carried by the shaft and is arranged to close the first and second clamps against the vessel at respective locations disposed adjacent one another. The displacement mechanism is also arranged for moving the first and second clamps in generally opposite directions to sever the vessel.

Preferably, each clamp includes at least one cauterizing pad for cauterizing the vessel.

BRIEF DESCRIPTION OF THE DRAWINGS

The objects and advantages of the invention will become apparent from the following detailed description of a preferred embodiment thereof in connection with the accompanying drawings in which like numerals designate like elements and in which:

FIG. 1 is a top plan view of a front end of an endoscopic vessel-harvesting device according to the present invention, the device being oriented in a relationship to be inserted into a patient.

FIG. 2 is a front perspective view of FIG. 1.

FIG. 10 is a front elevational view of the device, with the jaws being opened as shown in FIG. 6.

FIG. 11 is a side elevational view of the device, showing three different positions of an actuator sleeve.

FIG. 12b is a top plan view of FIG. 12a.

FIG. 13b is a top plan view of FIG. 13a.

FIG. 14b is a top plan view of FIG. 14a.

FIG. 15b is a top plan view of FIG. 15a.

DETAILED DESCRIPTION OF A PREFERRED EMBODIMENT OF THE INVENTION

Figure 3:
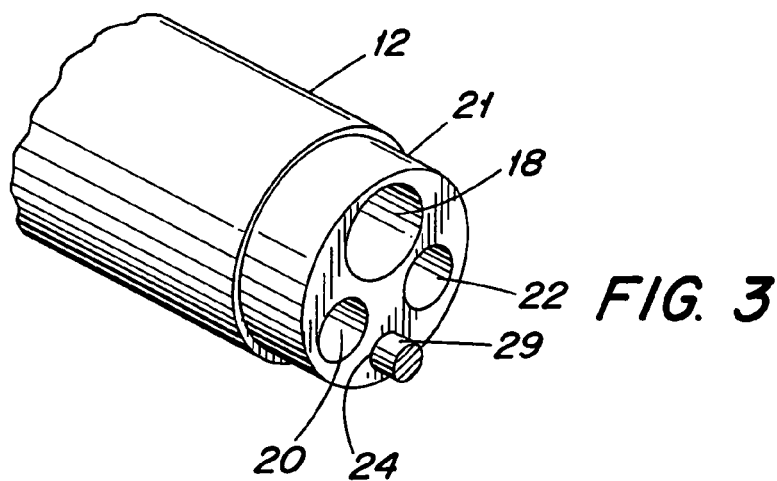
FIG. 3 is a front perspective view of a main portion of a shaft of the device depicted in FIG. 1.

An endoscopic vessel-harvesting device 10 according to the invention comprises a shaft 11 which includes a proximal section 12 and a distal section 16. The proximal section 12 includes four through-passages 18, 20, 22, 24 (see FIG. 3). The through-passage 18 accommodates the insertion of a conventional imaging system (not shown), comprising a lens arrangement connected to an optical fiber, to enable an operator to "see" objects of interest. The through-passages 20 and 22 accommodate left and right clamps in the form of jaw assemblies 26, 28, respectively (see FIG. 2). The through-passage 24 accommodates a rod 29 which is connected to the distal section 16 and serves to keep the distal section attached to the distal section 12.

Figure 5:
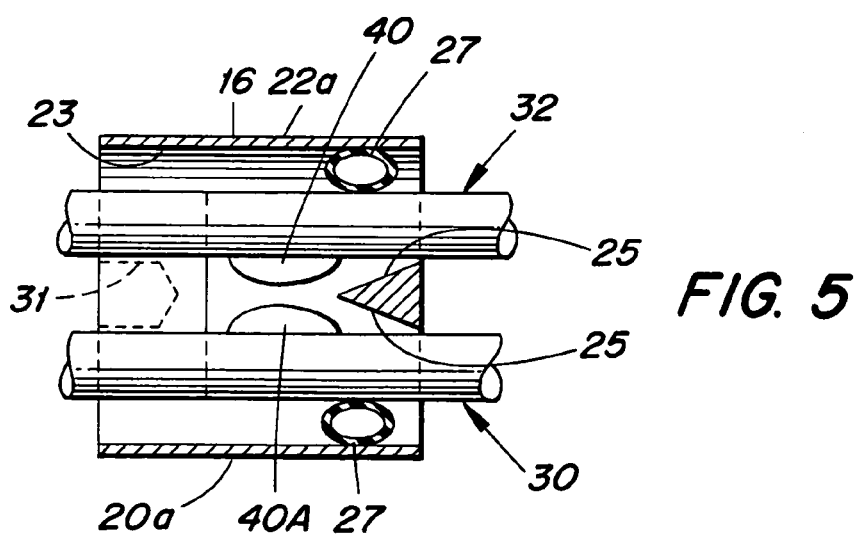
FIG. 5 is a longitudinal sectional view taken through a front portion of the shaft depicted in FIG. 1.

The distal section 16 includes three through-passages 18a, 20a, 22a (see FIGS. 2, 5). The through-passage 18a is aligned with the through-passage 18, and the through-passages 20a, 22a, are aligned with the passages 20, 22, respectively. The through-passages 20a, 22a open rearwardly into a cavity 23 that receives a reduced-diameter front end 21 of the proximal section 12 (see FIG. 5). The through-passages 20a, 22a include respective cam surfaces 25 and springs 27 at forward ends thereof for a reason to be explained.

The distal section 16 also includes a rearwardly open blind hole 31 aligned with the through-hole 24 (FIG. 5). The blind hole 31 has a female screw thread, for being threadedly connected to a male screw thread of the rod 29.

The jaw assemblies 26, 28 include slidable left and right sleeves 30, 32, respectively which function as jaw actuators as will be explained. The sleeves 30, 32 are of identical construction. The sleeves 30, 32 include respective cam followers 40A, 40 that face one another (see FIG. 5) and are arranged to interact with respective ones of the cam surfaces 25 disposed in the distal section 16 of the shaft 11, as will be explained.

The sleeve 30 includes an elongated cylindrical body 34 (FIG. 4) that extends through the passages 22, 22a to a rear end of the proximal section 12 so as to be slidable axially relative to the proximal section 12 by a force applied by an operator. The sleeve 30 also includes a socket 36 disposed at a front end of the body 34, the socket forming a cavity 38 of non-circular cross section i.e., preferably rectangular cross section. The open end of the socket 36 flares outwardly. A central channel 42 of smaller cross section than the cavity 38 extends through the body 34 and communicates with the cavity 38.

Mounted in the left sleeve 30 is a left jaw mechanism 52A of the left jaw assembly 26, and mounted in the right sleeve 32 is a right jaw mechanism 52 of the right jaw assembly 28 (see FIG. 5). Those jaw mechanisms 52, 52A are mirror images of one another.

Figure 4:
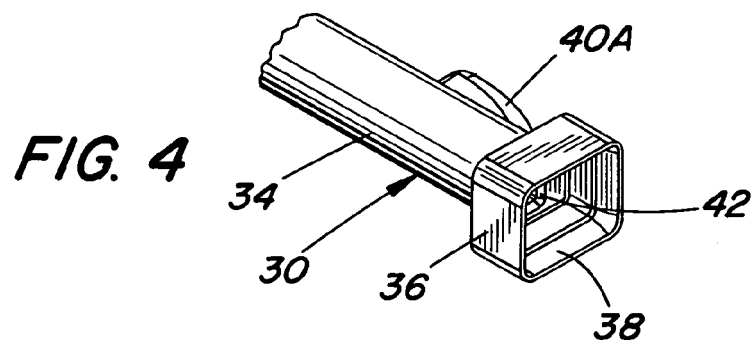
FIG. 4 is a front perspective view of an actuator sleeve forming part of the device depicted in FIG. 1.
Figure 6:
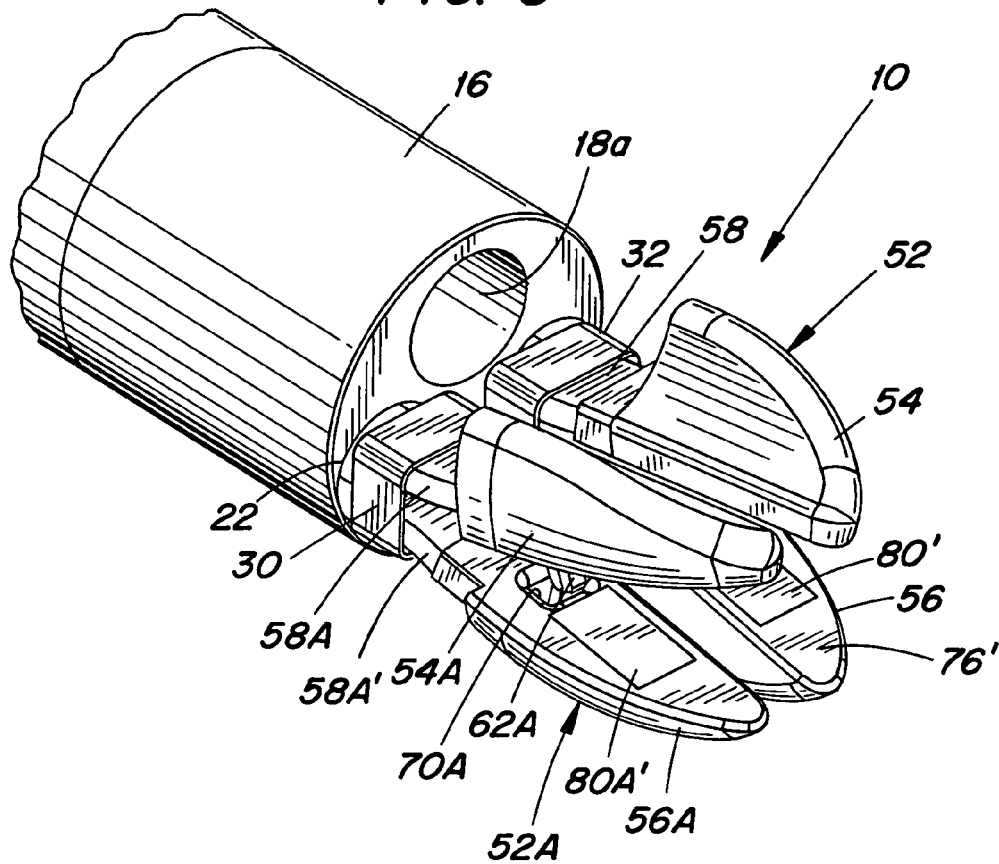
FIG. 6 is a view similar to FIG. 2 depicting jaws of the device in an open state.

The right jaw mechanism 52, depicted in FIGS. 4–6, includes a pair of jaws, i.e., an upper right jaw 54 and a lower right jaw 56. When in a closed state, the jaws 54, 56 form a generally conical, i.e., somewhat pointed shape. The upper right jaw 54 includes a rearwardly facing lug 59 that is mounted at the front end of a flexible base strip 58 (see FIG. 7) which extends through the channel 42 of the right sleeve 32. The base strip 58 is manipulatable by the operator, i.e., it can be slid forwardly and rearwardly within and relative to the sleeve 32. Projecting downwardly from the right upper jaw 54 is a tooth 62 (FIG. 8) for reasons to be explained.

The lower right jaw 56 is similar to the upper right jaw 54 in that it includes a rearwardly facing lug 59' mounted at the front end of a flexible base strip 58'. The lower right jaw 58' includes a recess 70 arranged for receiving the tooth 62 of the upper right jaw 58' to maintain the upper and lower right jaws 59, 56 in proper alignment (i.e., superimposed relationship as they open and close). Also, the tooth 62 limits the extent to which a blood vessel can move rearwardly relative to the jaws 54, 56, as will become apparent.

The lugs 59, 59' are configured such that both can be captured within the cavity 38 of the sleeve 32 when the jaws 54, 56 are closed.

Mutually facing surfaces of the strips 58, 58' are interconnected at a location behind the jaws 54, 56 by a spring 71 (FIG. 6). The opening (i.e., spreading apart) of the upper and lower jaws 59, 59' is performed automatically by the spring 71. The closing of the jaws 59, 59' is performed by moving the sleeve 30 forwardly relative to the shaft 11 and relative to the jaws, whereupon the strips 58, 58' are forced toward one another by the walls of the channel 42 as the spring 71 yields elastically.

Figure 7:
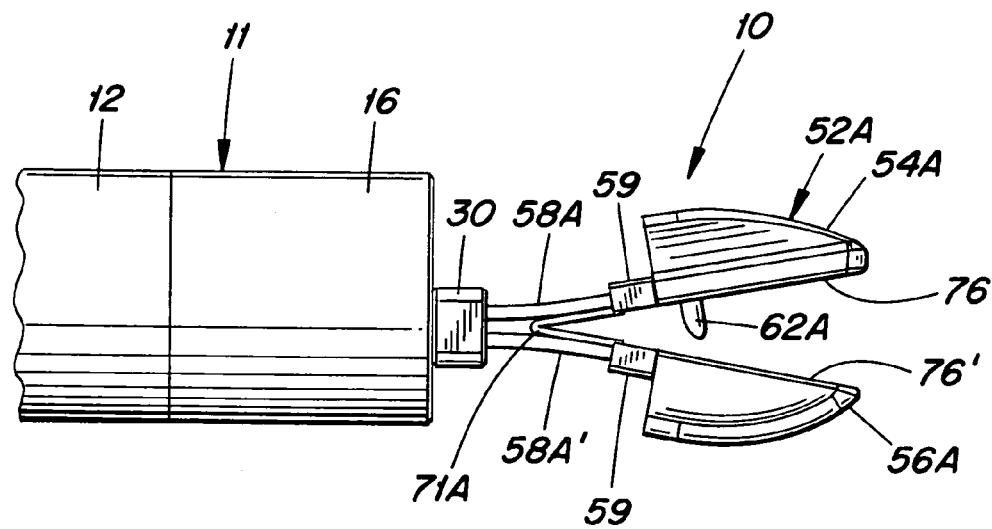
FIG. 7 is a side elevational view of FIG. 6.
Figure 8:
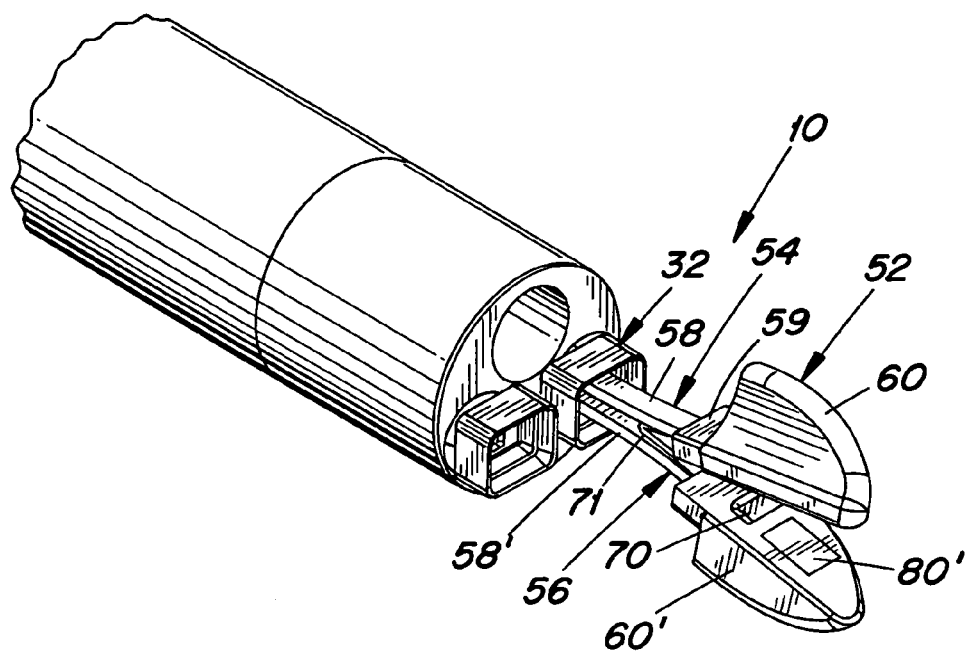
FIG. 8 is similar to FIG. 6 with one of two clamps removed for clarity.
Figure 9:
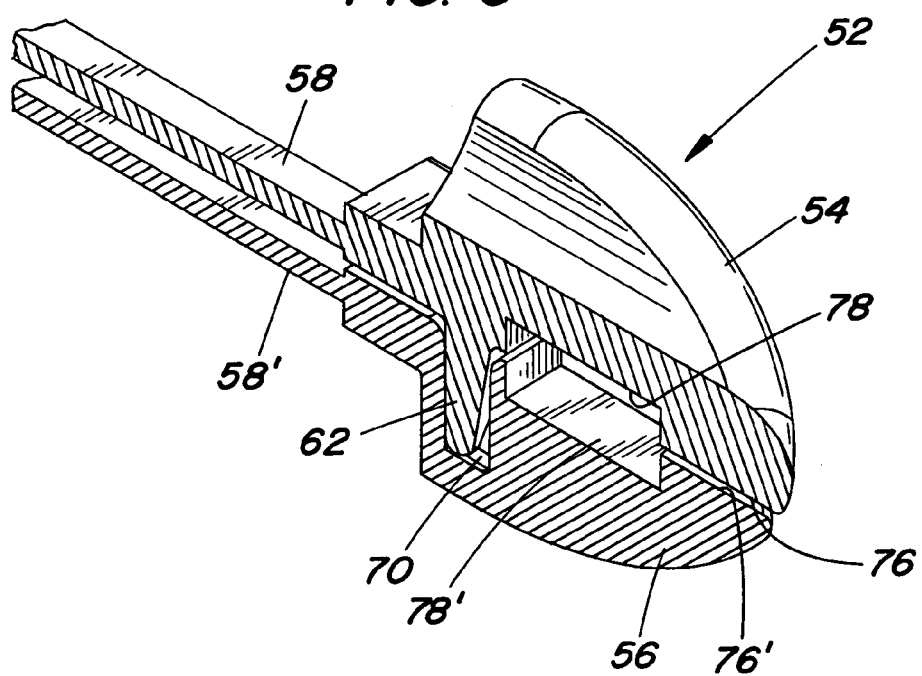
FIG. 9 is a sectional view, shown in perspective, of a clamp according to the present invention.

The jaws 54, 56 include mutually facing clamping surfaces 76, 76' (FIG. 7). Disposed in each of the clamping surfaces is a recess 78, 78' in which is mounted cauterizing pad 80, 80' (see FIGS. 6 and 10). Each cauterizing pad is electrically conductive and connected to a source of electric energy for cauterizing a severed end of a vessel as will be explained.

The left jaw mechanism 52A is a mirror image of the right jaw mechanism 52 in that it includes upper and lower left jaws 54A, 56A which include flexible carrying strips 58A, 58A'. Each jaw 54A, 56A has a cauterizing pad 80A, 80A' mounted therein. A spring 71A biases the jaws 54A, 56A open. A tooth-and-recess arrangement 62A, 70A keeps the jaws 54A, 56A in proper alignment.

Figure 12A:
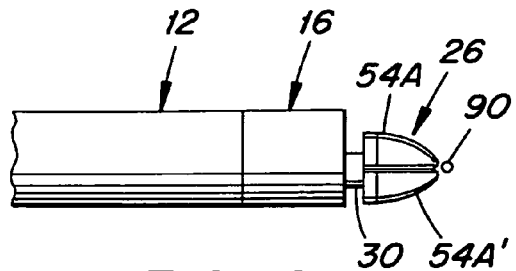
FIG. 12a is a side elevational view of the device shown in FIG. 1, as the device approaches a blood vessel to be severed.
Figure 12B:
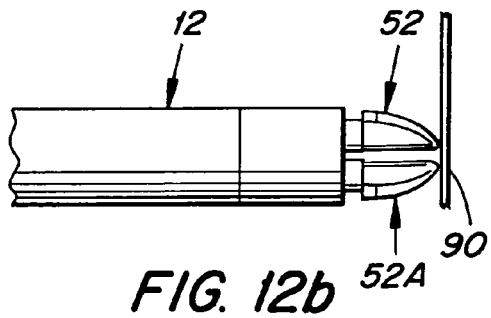
Figure 13A:
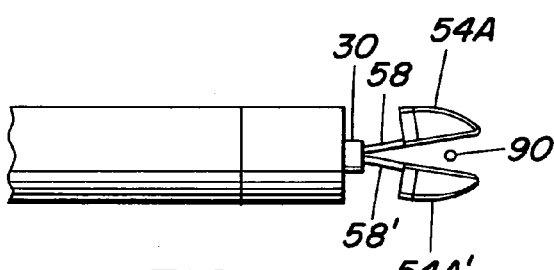
FIG. 13a is a view similar to view FIG. 12a after the clamp has been opened and encompasses the vessel.
Figure 13B:
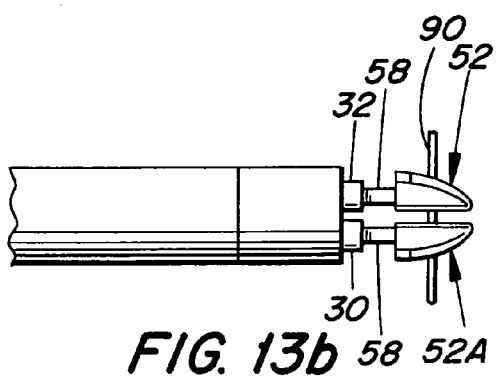

The operation of the device 10 to harvest a section of a saphenous vein will be explained, especially with reference to FIGS. 12–15. A small incision is formed at an appropriate location in a patient's leg adjacent the saphenous vein. The forward end of the device 10 is inserted through the incision and advanced toward an initial lateral branch 90 of the saphenous vein (FIGS. 12a, 12b). The pointed ends defined by the conical shape of the closed jaw mechanisms 52, 52A could be employed to perform blunt dissection of the tissue surrounding the saphenous vein. An imaging device (not shown) is disposed within the through-passages 18, 18a of the shaft 11 to enable the physician to maneuver the device 10 to orient the branch 90 transversely relative to the axis of the device 10. The right and left jaw mechanisms 52, 52A are advanced by sliding the base strips 58, 58', 58A, 58A' forwardly relative to the shaft 11 and relative to their respective sleeves 32, 30 (FIGS. 2, 6, 7, 10, 13, 13a), whereupon the springs 71, 71A open the jaws 54, 56 and 54A, 56A (e.g., to a 20 degree angle), causing the vein branch 90 to become situated between the opened jaws 54, 56 and 54A, 56A. The teeth 62, 62A of the jaw mechanisms 52, 52A serve not only to keep the jaw heads 60, 60' and 60A, 60A' is proper alignment, but also serve as stops to limit the extent to which the vein branch 90 can enter the jaws while simultaneously orienting the vein branch 90 between the cauterizing pads 80, 80' on the right side, and 80A, 80A' on the left side.

Figure 14A:
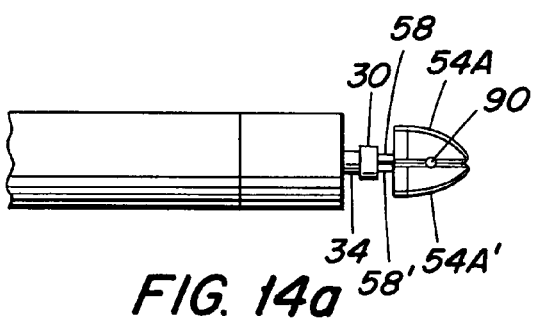
FIG. 14a is a view similar to FIG. 13a after an actuator sleeve has been moved from a first position to a second position in order to close the clamp against the vessel.
Figure 14B:
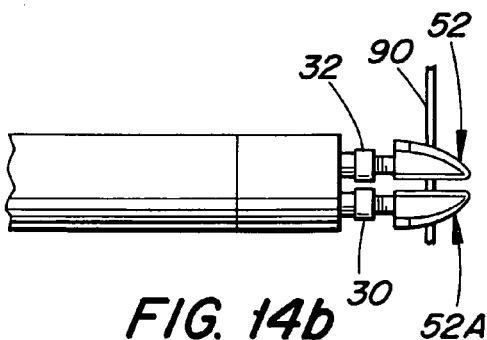

Then, the right and left sleeves 32, 30 are advanced relative to the shaft 11 and relative to the jaw mechanisms 52A, 52, to an intermediate position (i.e., the "socket position 2" in FIG. 11) wherein the sockets 36 are situated about midway between a front end of the actuator shaft 16 and a rear end of the jaws 54, 56 and 54A, 56A. That location is sufficiently far forward to cause the jaws 54, 56 and 54A, 56A to be forcibly closed to clamp against the vein branch 90 (FIGS. 14a, 14b). Simultaneously, the electrically heated cauterizing pads 80, 80' and 80A, 80A' cauterize the severed ends of the vein branch 90.

Figure 15A:
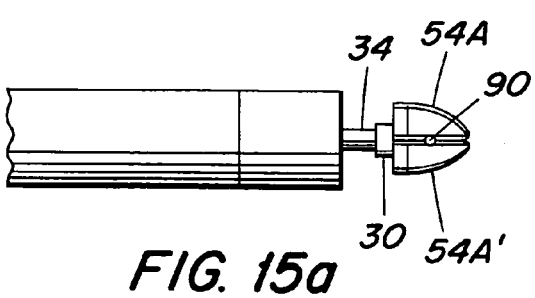
FIG. 15a. is a view similar to FIG. 14a after the actuator sleeve has been moved to a third position for moving the clamps away from one another.
Figure 15B:
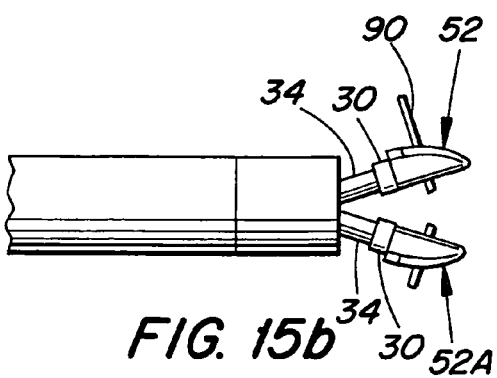

Thereafter, the sleeves 32, 30 are slid further forwardly to "socket position 3" in FIG. 11 to cause the cam followers 40, 40A to contact respective ones of the cam surfaces 25 of the shaft 11 (see FIG. 5), whereupon the sleeves 32, 30 are forcibly spread apart in a direction generally parallel to the vein branch (FIGS. 15a, 15b). This is possible, due to the flexibility of: the strips 58, 58', 58A, 58A', the sleeves 30, 32, and the springs 27 disposed in the through-passages 20a, 22a. As a result, the vein 90 branch is stressed and broken at a location between the jaw mechanisms, i.e., between the cauterized regions. Then, the sleeves 32, 30 are retracted (i.e., moved to the left in FIG. 6) to be biased back to a mutually parallel state by the springs 27, and to enable the jaws 54, 56 and 54a, 56a to be re-opened by the springs 70, 70A for releasing the severed sections of the lateral vein branch 90. The springs 27 can be of any suitable type, such as elastic oval elements.

If desired, the distal section 16 of the shaft 11 could be provided with a stop (not shown) that terminates forward movement of the sleeves 32, 30 at the "socket portion 3".

The device 10 is then advanced to cut the next lateral vein branch of the saphenous vein. When all of the lateral vein branches have been cut off, the device is actuated in the above-described manner to make two cuts in the saphenous vein to separate a section of the saphenous vein which is then removed through the incision for use in the coronary bypass procedure.

It will be appreciated that the invention enables a section of the saphenous vein to be harvested with a minimal number of instrument insertions and withdrawals relative to the patient's leg, thereby minimizing trauma to leg tissue.

Although the present invention has been described in connection with a preferred embodiment thereof, it will be appreciated by those skilled in the art that additions, deletions, modification, and substitutions not specifically described may be made without departing from the spirit and scope of the invention as defined in the appended claims.

What is claimed is:

1. A method of severing a blood vessel in a patient comprising the steps of:
   A. inserting a shaft through an incision in the patient, the shaft carrying first and second clamps, each clamp including a pair of base strips, each base strip carrying a jaw at a forward end thereof, the jaws being spring biased away from one another: the shaft carrying a pair of sleeves slidably disposed in the shaft, the pair of base strips of each clamp being slidably disposed within a respective one of the sleeves;
   B. applying the first and second clamps to the vessel in closely adjacent relationship by forwardly sliding the sleeves relative to both the shaft and the respective strips from a first position to a second position wherein the sleeves force respective pairs of jaws closed; and then
   C. moving the first and second clamps in generally opposing directions to sever the vessel at a location between the clamps by forwardly sliding the sleeves relative to both the shaft and both strips from the second position to a third position, wherein the sleeves and their respective strips are forced away from one another.

2. The method according to claim 1 wherein step C is performed by moving the first and second clamps away from one another generally along a longitudinal axis of the vessel.

3. The method according to claim 1 further comprising the step of contacting portions of the blood vessel with cauterizing pads carried by the clamps, wherein the blood vessel is cauterized on opposite sides of the location of severing.

4. The method according to claim 1 wherein step C is further performed by causing cam followers carried by respective sleeves to contact cam surfaces disposed in the shaft during travel of the sleeves from the second position to the third position.

5. The method according to claim 1 further including, between steps A and B, the step of utilizing generally pointed ends of the clamps to perform blunt dissection of tissue surrounding the vessel.

* * * * *